United States Patent [19]

Loudas

[11] 4,160,777

[45] * Jul. 10, 1979

[54] FLUOROCHEMICAL COMPOUND USEFUL FOR TEXTILE TREATMENT

[75] Inventor: Basil L. Loudas, St. Paul, Minn.

[73] Assignee: Minnesota Mining and Manufacturing Company, St. Paul, Minn.

[ * ] Notice: The portion of the term of this patent subsequent to Aug. 23, 1994, has been disclaimed.

[21] Appl. No.: 759,467

[22] Filed: Jan. 14, 1977

Related U.S. Application Data

[62] Division of Ser. No. 446,003, Feb. 26, 1974, Pat. No. 4,043,923.

[51] Int. Cl.[2] .................. C07C 143/68; C07C 143/74; C07C 101/04

[52] U.S. Cl. ................................ 260/456 F; 560/227; 562/426; 562/451; 562/455; 562/507; 562/556; 562/574

[58] Field of Search ............ 260/456 F, 518 A, 534 S, 260/514 G, 514 J, 517, 456 F; 560/150, 227; 562/426, 451, 455, 556, 507, 574

[56] References Cited

U.S. PATENT DOCUMENTS

| | | | |
|---|---|---|---|
| 2,809,990 | 10/1957 | Brown | 260/534 S |
| 2,934,450 | 4/1960 | Brown | 260/534 S |
| 3,238,235 | 3/1966 | Hauptschein et al. | 260/456 F |
| 3,639,474 | 2/1972 | Harrington et al. | 260/518 A |
| 3,697,562 | 10/1972 | Beyleveld et al. | 260/518 A |
| 3,754,026 | 8/1973 | Beyleveld et al. | 260/518 A |
| 3,852,313 | 12/1974 | Beyleveld et al. | 260/518 A |
| 4,043,923 | 8/1977 | Loudas | 252/8.75 |

*Primary Examiner*—Nicky Chan

*Attorney, Agent, or Firm*—Cruzan Alexander; Donald M. Sell; Richard Francis

[57] ABSTRACT

Textiles, particularly carpets, are endowed with oil and water repellency and soil resistance by treatment thereof with certain detergent-compatible fluorochemical compounds which can also be used in conjunction with anionic or nonionic detergents to provide cleaning/treating compositions for cleaning such textiles simultaneously with the treatment. The textile treating compositions of the invention comprise certain detergent-compatible fluorochemical compounds which are dissolved and/or dispersed in a suitable liquid vehicle. The textile treating/cleaning compositions of the invention also contain an anionic and/or a nonionic detergent.

4 Claims, No Drawings

FLUOROCHEMICAL COMPOUND USEFUL FOR TEXTILE TREATMENT

CROSS-REFERENCE TO RELATED APPLICATION

This is a division of copending application Ser. No. 446,003, filed Feb. 26, 1974, now U.S. Pat. No. 4,043,923.

BACKGROUND OF THE INVENTION

This invention relates to textile treatment with novel compositions to impart water and oil repellency and soil resistance. In another aspect, the invention relates to cleaning/treating compositions for cleaning such textiles simultaneously with such treatment.

DESCRIPTION OF THE PRIOR ART

The treatment of textiles with fluorochemicals to impart water and oil repellency has been known for some time. As disclosed in U.S. Pat. Nos. 3,068,187; 3,256,230; 3,256,231; 3,277,039; and 3,503,915, fluorinated polymers have been mixed with non-fluorinated polymers to obtain a treating composition which will impart water and oil repellency to textiles, paper and leather. Such prior art compositions, however, are generally designed for initial factory treatment of the textile and are not suited for use after the textile article has been soiled in use.

U.S. Pat. No. 3,377,197 discloses treating previously cleaned textile fabric, leather, rugs, etc., with fluorine-containing organometallic compounds to impart resistance against soiling, staining and wetting. U.S. Pat. No. 3,382,097 discloses a treatment for imparting oil and soil repellency to textile fabric, leather, rugs, etc., by treating with a solution of certain fluorinated organic carboxylic acids. This reference also suggests combining a detergent with a fluorochemical acid in an aqueous medium for a one-step cleaning and treating operation, but it does not impart water repellency. And, although Netherlands patent application No. 6,606,734 suggests dispersing an insoluble fluorocarbon compound in a laundering composition useful for a two-step cleaning operation, such disclosure does not provide a one-part treating/cleaning composition.

Other prior art cleaning compositions, such as carpet shampoos, do not impart water and oil repellency. Rather, many such conventional cleaning compositions leave hydrophilic or oleophilic residues on the cleaned substrate which actually attract and hold dirt. Although some cleaning compositions contain ingredients designed to impart soiling resistance, such compositions do not impart water and oil repellency.

SUMMARY OF THE INVENTION

The present invention provides novel compositions for the fluorochemical treatment of textiles such as carpets, upholstery and the like, to impart water and oil repellency and stain resistance thereto. Quite surprisingly, these novel compositions can also contain detergent and thereby clean and impart repellent properties in one operation.

In accordance with the invention, a textile treatment is provided by certain detergent-compatible organic fluorochemical compounds. The textile treating compositions of the invention comprise certain detergent-compatible fluorochemical compounds which are dissolved and/or dispersed in a suitable liquid vehicle. The textile treating/cleaning compositions of the invention also contain an anionic and/or a nonionic detergent. The term "detergent compatible" is used herein to denote that the organic fluorochemical compounds are physically and chemically unaffected by anionic and nonionic detergents at concentrations thereof typically encountered in textile cleaning solutions, and thus capable of being applied during a cleaning operation. Additionally, the organic fluorochemical compound treatment, applied to a substrate such as a carpet, can be cleaned with conventional carpet-cleaning detergent-containing solutions without removing or rendering ineffective the organic fluorochemical, provided that excessive detergent residue does not remain.

DETAILED DESCRIPTION

The detergent-compatible organic fluorochemical compounds that are useful in the invention are those in which a fluorinated, preferably saturated, aliphatic radical is linked to a non-fluorinated organic radical which bears at least one carboxylic acid group which may be neutralized. The non-fluorinated organic radical has at least 6 members (e.g., carbon atoms) in a skeletal backbone structure which links the fluoroaliphatic radical to the carboxylic acid group. This skeletal structure can include catenary oxygen and/or trivalent nitrogen hetero atoms, providing a stable linkage between the fluoroaliphatic radical and the carboxylic acid group. These fluorochemical compounds are capable of dissolving in an organic solvent, preferably in a water-soluble or water-dispersible organic solvent.

The fluoroaliphatic radicals, hereinafter called "$R_f$ radicals", are saturated, and generally monovalent aliphatic moieties. They can be straight chain, branched chain, and, if sufficiently large, cyclic, or combinations thereof, such as alkylcycloaliphatic radicals. The fluoroaliphatic skeletal chain can include catenary oxygen and/or trivalent nitrogen hetero atoms bonded only to carbon atoms, such hetero atoms providing stable linkages between fluorocarbon groups and not interfering with the inert character of the $R_f$ radical. While $R_f$ can have a large number of carbon atoms, $R_f$ radicals having no more than 20 carbon atoms will be adequate and preferred since larger radicals usually represent a less efficient utilization of fluorine than is possible with smaller $R_f$ radicals. Generally, $R_f$ will have 3 to 20 carbon atoms, preferably 6 to about 12, and will contain 40–78 weight percent, preferably 50–77 weight percent, carbon-bonded fluorine. The terminal portion of the $R_f$ radical has preferably at least one fully fluorinated carbon atom, e.g., $CF_3$, and the preferred $R_f$ radical is substantially completely, or fully fluorinated, as in the case where $R_f$ is perfluoroalkyl, $C_nF_{2n+1}$.

Generally, the detergent-compatible organic fluorochemical compounds will contain about 10 to 60 weight percent, preferably about 15 to 45 weight percent, of carbon-bonded fluorine. If the fluorine content is less than about 10 weight percent, these compounds may no longer be detergent compatible, while fluorine contents greater than about 60 weight percent will require compounds which are uneconomical to use.

Suitable liquid vehicles for the compositions of the invention will dissolve or disperse the detergent-compatible fluorochemical. The preferred liquid vehicles are organic solvents or organic solvent/water mixtures. The organic solvents for this purpose are volatile at room temperature and will preferably be capable of dissolving and/or dispersing 1 part detergent-compatible fluorochemical compound per 10 parts organic solvent and preferably will dissolve and/or disperse in water at least 1 part organic solvent per 10 parts water. The organic solvents are non-toxic, do not have an odor which is objectionable to the normal person and do not harm carpet fibers or structure.

Organic fluorochemical compounds which are detergent compatible and preferred in the present invention have the structure: $(R_fQ)_e(XCO)_mA(COOM)_p$ wherein $R_f$ is fluorinated aliphatic radical as described above, "Q" is a divalent linking group, "M" is a cation selected from $NH_4^+$, $Na^+$, $K^+$, $Li^+$, $H^+$, or a protonated alkyl amine having from 1-6 carbon atoms in the alkyl group, "A" is a polyvalent organic radical having a valency of m+p and is preferably derived from a polybasic organic acid or an organic anhydride, "X" is NR (wherein "R" is hydrogen or a lower alkyl group of from 1 to 14 carbon atoms), N or O, "e", "p" and "m" are integers of 1 or 2.

It should be noted that because of the polyvalent nature of the "A" group, the fluorochemical compounds may be a polyanhydride polymer structure having repeating structure

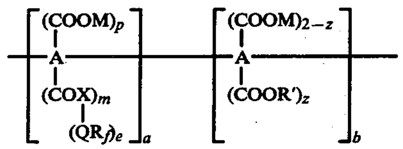

wherein "R'" is alkyl of from 1-6 carbon atoms or alkoxy alkyl such as butoxyethyl, ethoxyethyl, etc, "z" is from zero to 1, "b" is from zero to 10 times "a" and "a" plus "b" is an integer representing the number of repeating units in the polymer.

The divalent linking group "Q" has a valency of 2 and may include one or more groups such as alkylene $[-(CH_2)_n-]$,

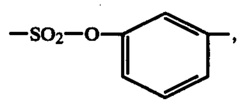

$-SO_2(C_2H_5)C_2H_4NHC_2H_4-$, sulfonamido alkylene $[-SO_2NR_1(CH_2)_n-]$, alkylene carboxyloxy alkylene $[-(CH_2)_nCOOCH_2CH_2-]$, and sulfonamido alkyleneoxy alkylene $[-SO_2NR_1(CH_2CH_2O)_nCH_2CH_2-]$ wherein "$R_1$" is hydrogen or a lower alkyl group having from about 1 to 14 carbon atoms and "n" is an integer from about 1 to 15.

The polyvalent organic radical "A" has, as previously mentioned, a valency of "m" to "p" and may be aromatic, araliphatic, cycloaliphatic or heteroaromatic and is preferably the residue of a polybasic acid or an anhydride from which the carboxyl groups have been deleted. Such anhydrides and acids include maleic, succinic, phthalic, tetrachlorophthalic, chlorendic, tetrabromophthalic, 3-nitrophthalic, 4-nitrophthalic, cis 1,2-cyclohexane dicarboxylic, 5-norbornene-2,3-dicarboxylic, 1,8-naphthalene dicarboxylic and benezophenone tetracarboxylic and others.

The detergent-compatible organic fluorochemical compounds described above and useful in the present invention may be prepared in any of a variety of ways. Most conveniently, the compounds which are preferred in the invention are prepared by reacting a precursor fluorochemical amine or alcohol with a suitable anhydride. Precursor amines and alcohols will have the structure $R_fQXH$ where "$R_f$", "Q" and "X" are as described above. Useful illustrative examples of such precursor amines and alcohols include:

$CF_3(CF_2)_7SO_2N(CH_3)CH_2CH_2OH$
$CF_3(CF_2)_3SO_2N(CH_3)CH(CH_3)CH_2OH$
$CF_3(CF_2)_3SO_2N(CH_2CH_3)CH_2CH_2OH$
$CF_3(CF_2)_3SO_2N(CH_3)CH_2CH(CH_3)OH$
$CF_3(CF_2)_7SO_2N(CH_2CH_3)CH_2CH_2OH$
$CF_3(CF_2)_9SO_2N(CH_2CH_2CH_3)CH_2CH_2OH$
$CF_3(CF_2)_7SO_2N(CH_2CH_2CH_3)CH_2CH_2OH$
$CF_3(CF_2)_7SO_2N(C_2H_5)(CH_2)_6OH$
$CF_3(CF_2)_7SO_2N(C_2H_5)(CH_2)_{11}OH$
$CF_3(CF_2)_7SO_2N(C_4H_9)(CH_2)_4OH$
$CF_3(CF_2)_7SO_2N(CH_3)(CH_2)_4OH$
$CF_3(CF_2)_7SO_2N(CH_2CH_3)CH_2CH_2NH_2$
$[CF_3(CF_2)_7SO_2N(CH_2CH_3)CH_2CH_2]_2NH$
$CF_3(CF_2)_7SO_2N(CH_2CH_3)CH_2CH_2N(CH_3)H$
$CF_3C_6F_{10}C_2F_4SO_2N(CH_3)CH_2CH_2OH$
$C_2F_5O(C_2F_4O)_3CF_2CONHC_2H_4OH$
$CF_3(CF_2)_7SO_2N(C_3H_7)CH_2OCH_2CH_2CH_2OH$

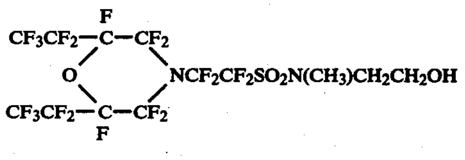

$CF_3(CF_2)_6SO_2CH_2CH_2OH$
$CF_3(CF_2)_6COCH_2CH_2OH$
$C_7F_{15}CON(C_2H_5)C_2H_4OH$
$C_8F_{17}SO_2N(C_4H_9)CH_2CH_2OH$
$C_7F_{15}CON(CH_3)CH_2CH_2OH$
$C_8F_{17}SO_2NH(CH_3)(CH_2)_4OH$
$C_8F_{17}SO_2N(CH_3)(CH_2)_{11}OH$
$C_6F_{13}SO_2NCH_3(CH_2)_4OH$

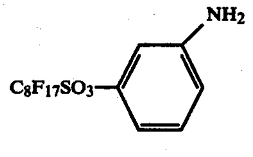

$C_7F_{15}CH_2NH_2$
$C_8F_{17}SO_2N(C_4H_9)CH_2CH_2NH_2$

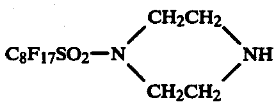

$C_8F_{17}SO_2N(C_2H_5)CH_2CONHCH_2CH_2NH_2$
$C_8F_{17}SO_2N(C_2H_5)CH_2CH_2NHCH_2CH_2NH_2$

Many of the precursor fluorochemical amines and alcohols are well known and/or commercially available. U.S. Pat. No. 3,346,612 discloses a method of preparing the fluorochemical amines while U.S. Pat. No. 3,398,182 discloses some useful amines and alcohols.

In the reaction which produces the preferred detergent-compatible organic fluorochemical compound, the precursor fluorochemical amine or alcohol is reacted usually with about an equivalent amount of the anhydride. In certain instances, e.g., the polyanhydride polymers previously mentioned, the ratio (by equivalents) of amine or alcohol to anhydride may vary between 1:10 and 1:1. This reaction is most conveniently accomplished in a solvent for both the reactants and the reaction product. Typical solvents for the precursor fluorochemical amine are water miscible and include dimethyl formamide, dimethyl acetamide and N-methyl pyrrolidone, ketones such as acetone or methyl ethyl ketone, ethers such as tetrahydrofuran, and alkoxy ethanols, such as 2-ethoxy ethanol or 2-butoxy ethanol (e.g. "Butyl Cellosolve"). Preferred solvents for the precursor alcohols are aprotic and include dimethyl formamide dimethyl formamide, dimethyl acetamide, N-methyl pyrrolidone, pyridine and triethylamine.

When the precursor alcohol or amine is dissolved in an aprotic solvent, a minimum amount thereof to dissolve the reactants is used, since these solvents are generally removed before using the reaction product in a textile treatment.

The dissolved precursor fluorochemical amine is typically reacted with the anhydride by slowly adding the latter to a solution of the former with sufficient agitation to obtain uniform dispersal. Reaction times are relatively short and the reactions are typically carried out at temperatures in the range of about 20° C.–80° C. and at atmospheric pressures. An ambient (air) reaction atmosphere may be used but dry nitrogen is preferred.

It has been found that if the reaction temperatures are maintained between about room temperature (20° C.) and 80° C., a high yield of the desired organic fluorochemical compound is produced with minimal side products from secondary reaction. If the temperature is elevated above 85° C., some reaction of the anhydride and solvent may occur or the amide may partly cyclize, reducing the water solubility of the resultant compounds which may be undesirable in some instances.

Fluorochemical alcohols may be reacted with the anhydride by direct melt esterification or in the presence of aprotic solvents, preferably with esterification promoting catalysts such as perfluoromethane sulfonic acid or a tertiary amine.

Once the reaction has been completed to produce the desired detergent-compatible fluorochemical compound, if the solvent used is undesirable for the final water dilution (because of being slow drying, having a bad odor, etc.), the product may be removed from the reaction solvent for example by precipitating it therefrom with an aqueous acid solution. The precipitate is then dissolved and/or dispersed in the liquid vehicle.

The resultant fluorochemical compound product, which has a free carboxylic acid group, may be neutralized with a slight excess of a base to make it water-soluble or water-dispersible. Suitable bases for this purpose are at least moderately water-soluble and include ammonia, potassium hydroxide, sodium hydroxide, morpholine or an alkylamine such as triethylamine, propylamine, ethylamine, isopropylamine, isobutylamine, butylamine, ethanolamine, diethanolamine, diethylaminoethanol, 2-amino-2-ethyl propanol, etc.

The term "dispersible" as used herein means that the ingredients of the mixture either are mutually soluble, or otherwise stably dispersible, e.g., forming a colloidal suspension in water at the desired concentration.

The organic solvent either dissolves the acidic fluorochemical compounds or aids in the water-dispersibility of the neutralized fluorochemical compound, providing aqueous treating or treating/cleaning compositions which are preferred. The preferred ratio of organic fluorochemical compound to organic solvent is on the order of 1:1 to 1:5, by weight. Organic solvents which may be utilized include ethanol, alkoxy-ethanols such as 2-ethoxy or 2-butoxy ethanol, tetrahydrofuran, methyl ethyl ketone, acetone, dimethyl formamide etc, and mixtures thereof. Organic solvents having no or limited water-solubility, e.g., hexoxy ethanol, may be used in minor proportions with organic solvents which are more water-soluble.

The solutions of fluorochemical compound, water and solvent described above, when applied to clean or previously cleaned textile materials and dried, provide a high degree of water and oil repellency and soil resistance. Not only is such repellency provided, but the treated textile may be subsequently cleaned with common detergent-containing textile cleaning solutions and still thereafter retain these repellency properties if most of the detergent is removed (e.g., by means of wet-vacuuming).

Typical concentrations of the organic fluorochemical compound will be on the order of about 10 to 25 weight percent by weight fluorochemical compound per total weight of a concentrated solution, depending upon its solubility. For use, the concentration of organic fluorochemical compound will be on the order of 1 to 2% by weight. Excellent water and oil repellency and stain resistance are obtained on carpeting having an add-on weight of at least 1 g per sq. meter of fluorochemical compound, preferably 2–5 grams per sq. meter.

It should be noted that certain of the detergent-compatible fluorochemical compounds of the invention, i.e., where "X" in the general formula noted above is nitrogen, will be endowed with improved repellency properties upon being heated at an elevated temperature, e.g., over 100° C., preferably at about 125° C. One example is the fluorochemical compound produced as described above by reacting a dicarboxyic anhydride and a primary fluorochemical amine, as the acid or neutralized with base such as ammonia or morpholine. Heating times sufficient to note this improvement will typically be between 10 minutes and 5 hours. This further treatment may be accomplished on the textile surface during its production, by treating the textile with the treating compositions described above and by heating the treated textile.

As previously mentioned, the solution may be a cleaning/treating composition containing a detergent. The detergents should be water-dispersible at concentrations of at least 1% by weight. Detergents which are useful in such compositions are nonionic or anionic detergents which dry to a non-oily, non-tacky residue from an aqueous medium. Solid detergents which leave a dry residue are desirable. Cationic detergents are not useful because they are not generally compatible with the other ingredients in the compositions.

Useful anionic detergents include alkali metal or ammonium salts of fatty acids (e.g., 12 carbons or more), alcohol sulfates (or sulfonates), alcohol phosphates (or phosphonates), alkyl sulfonates, alkyl phosphates (or phosphonates), polyoxyalkylene alcohol sulfates (or sulfonates), polyoxyalkylene alkyl carboxylates, and polyoxyalkylene alcohol phosphates (or phosphonates).

Examples of commercial anionic detergents that are useful in the invention include sodium lauryl sulfate (commercially available under the trade designation "Avirol" 101), potassium lauryl sulfate (commercially available under the trade designation "Culverol" KLS), magnesium lauryl sulfate (commercially available under the trade designation "Culverol" MgLS), sodium myristyl sulfate (commercially available under the trade designation "Maprofix" MSP90), sodium cetyl sulfate (commercially available under the trade designation "Conco" Sulfate A), sodium tridecyl sulfate (commercially available under the trade designation "Sipex" TDS), sodium 7-ethyl-2 methyl-4 undecyl sulfate (commercially available under the trade designation "Tergitol" 4). Of these, sodium lauryl sulfate is the preferred detergent.

Nonionic detergents, either by themselves or in conjunction with anionic detergents, can also be used in the cleaning/treating compositions. When nonionic detergents are used, it is preferred that they be normally solid materials, or if not solid, that they be used in amounts less than about 20% by weight of the total solids in the cleaning/treating solution. Useful commercial nonionic surfactants include "Igepal DM-970" and "Pluronic F 68".

The weight ratio of detergent to organic fluorochemical compound is on the order of 1:1 to 2:1, by weight. At more than 2:1 detergent to organic fluorochemical compound, some reduction in the water repellency properties of carpet treated with the organic fluorochemical compound may be noted.

The treating or cleaning/treating composition of the invention may contain other ingredients which increase effectiveness or improve physical appearance. For example these compositions may contain an additional known anti-redeposition agent. A typical example of such an anti-redeposition agent is the ammonium salt of the hydrolyzed copolymer of styrene and maleic anhydride. Other useful anti-redeposition agents include polyvinyl pyrolidone and water dispersible acrylate copolymers. Other optional additives include germicidal materials, perfumes and the like.

In use, the diluted cleaning/treating compositions are typically applied to the surface being cleaned and treated using conventional equipment. For example, for carpet cleaning, a conventional scrubbing device, which may be fitted with a liquid dispenser, is used, the cleaning/treating solution being dispensed from such a dispenser. The cleaning/treating and the treating solutions of this invention may be sprayed upon the surface to be cleaned and/or treated by conventional spraying devices or as an aerosol. The aerosol dispensing container will contain the desired solution and sufficient aerosol propellent to dispense the solution. Such propellents are typically low boiling chloro-, fluoro-substituted alkanes (e.g., "Freon 12") or low boiling alkanes or mixtures thereof such as a mixture of isobutane and propane.

Compositions according to the invention were applied to various textile substrates, typically carpeting of synthetic fibers, and the treated substrates were evaluated for oil and water repellency, as follows:

OIL REPELLENCY TEST

The test for oil repellency (which is similar to the method described in AATCC Test No. 118-1966T) involves wetting the fabric by a selected series of liquid hydrocarbons of different surface tensions. The test liquids are as follows:

| Oil Repellency Rating Number | Test Liquid |
|---|---|
| 1 | "Nujol" |
| 2 | 65:35 "Nujol":n-hexadecane by volume |
| 3 | n-hexadecane |
| 4 | n-tetradecane |
| 5 | n-dodecane |
| 6 | n-decane |
| 7 | n-octane |
| 8 | n-heptane |

"Nujol" is the trademark of Plough, Inc., for a mineral oil having a Saybolt viscosity 360/390 at 38° C. and a specific gravity 0.880/0.900 at 15° C.

In the test, one test specimen, approximately 20×20 cm, is conditioned for a minimum of four hours at 21°±1° C. and 65±2% relative humidity prior to testing. The test specimen is then placed on a smooth, horizontal surface and, beginning with the lowest-numbered test liquid, a small drop—approximately 5 mm in diameter (0.05 ml. volume)—is placed with a dropping bottle pipette on the test specimen in several locations. The dropping bottle pipette is a 60 ml. dropping bottle with a ground-in pipette and "Neoprene" rubber bulb. (Prior to use, the bulb should be soaked in heptane for several hours and rinsed in fresh heptane to remove soluble substances.) The drop is observed for 30 seconds at an angle of approximately 45°.

If no penetration or wetting of the fabric at the liquid-fabric interface and no wicking around the drop occurs, a drop of the next higher-numbered test liquid is placed at a site adjacent on the fabric to the first drop, again observing the drop for 30 seconds. This procedure is continued until one of the test liquids shows obvious wetting of the fabric under or around the drop within 30 seconds. An untreated nylon tufted pile carpet has an oil repellency of zero. The same carpeting treated with the treatment of the invention has an oil repellency up to 6.

WATER REPELLENCY TEST

The treated carpet is tested for water repellency, after it is dried for at least 4 hours at room temperature (about 20° C.) and under ambient laboratory humidity conditions (about 55% relative humidity).

One drop of room temperature tap water (about 2-3 mm in diameter) is then carefully applied utilizing an eye dropper held about 1 cm from the fiber surface which will receive it. The test is repeated on an adjacent area with a drop of an isopropyl alcohol/water solution (10/90% by weight). The drop is observed and one of the following ratings given, depending upon the observations:

| Rating | Observations |
|---|---|
| excellent | The water drop does not wet the surface and remains almost spherical in shape for at least 2 hours. The isopropyl alcohol/water solution drop remains on the fiber surface for at least 1 hour. |
| good | The water drop remains on the fiber surface for at least 1 hour with practically no wetting although the shape may not be spherical. The isopropyl alcohol/water solution remains at least 10 minutes before penetrating the fiber. |
| fair | The water drop may wet the upper surface of the fiber but does not substantially penetrate the bulk of the carpeting for at least ½ hour. The isopropyl alcohol/water solution penetrates the bulk of the carpeting almost immediately. |
| poor | Both the water and the alcohol solution |

-continued

| Rating | Observations |
|---|---|
| | immediately penetrate the bulk of the carpet |

Untreated nylon carpeting samples generally have a poor to fair water repellency while the same carpet treated with compositions according to the invention have a water repellency of fair to excellent. The fair rating of an untreated carpet, typically temporary, is usually caused by oily residues which are usually on a new carpet surface. A permanent fair water repellency is acceptable for a carpet treatment.

The invention is illustrated by the following examples, wherein all parts are by weight unless otherwise specified.

EXAMPLE 1

The organic fluorochemical compound

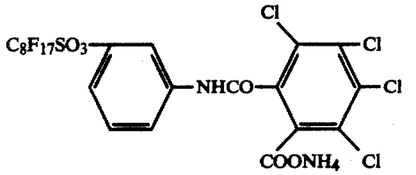

was prepared by reacting tetrachlorophthalic anhydrice (hereinafter called "TCPA" and sold under the trade designation "Tetrathal") with the fluorochemical amine, m-aminophenolperfluorooctane sulfonate,

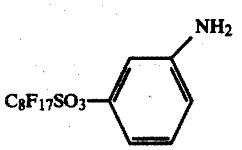

and neutralizing with ammonia. Twenty-five parts of TCPA was suspended in 75 parts of dimethyl formamide, the suspension heated to about 50° C. and 5 parts of triethylamine added, producing a reddish-brown color. Next, 50 parts of the fluorochemical amine was added with mixing and continued heating at 50° C., producing a clear solution which was cooled to room temperature. The slightly soluble monocarboxylic acid derivative was produced and isolated by diluting the clear solution with about 6 volumes of a dilute acetic acid solution, causing this derivative to precipitate as a white solid. The precipitate was filtered, washed with distilled water and air dried at room temperature.

The desired organic fluorochemical compound treatment concentrate was prepared by dissolving and neutralizing the acid derivative (about 1.0 part) in a solution consisting of 0.5 parts ammonia, 3.0 parts "Butyl Cellosolve" and 5.5 parts water.

This treatment concentrate was diluted with about nine volumes of water and the resultant solution was applied to a previously cleaned, rinsed and dried 2 foot square tufted looped pile nylon carpet test sample and permitted to dry overnight, producing a dried add-on weight of 5.4 grams/$m^2$. The treated carpet, when tested for oil and water repellency as described above, had an oil repellency of 5 and a water repellency rating of "excellent".

EXAMPLE 2

18 parts of TCPA was reacted with 50 parts of fluorochemical amine, m-aminophenol-perfluorooctane sulfonate. The fluorochemical amine was mixed with 130 parts of "Butyl Cellosolve" in the reaction flask and the mixture heated to about 60° C. until clear. Then, the TCPA was added in one lot and the mixture heated to about 70° C. with continued stirring. When the reaction mixture became clear, heat was discontinued and 20 parts of ammonium hydroxide solution (28% $NH_3$) was added followed immediately by a mixture of 330 parts of deionized water and 10 parts of chelating agent solution ("Versenol-120") with stirring. ("Versenol-120" is water solution containing 41.0% trisodium salt of N-hydroxy-ethyl ethylene diamine triacetic acid.) Then, 300 parts of a 10% by weight aqueous solution of styrene/maleic anhydride copolymer ("SMA-3000"), hydrolyzed with ammonia, anti-redeposition agent was added followed by 130 parts of detergent solution ("Richonol A", 30% sodium lauryl sulfate), 5 parts of fluorochemical surfactant ("FC 128") with heating to about 95°, giving a clear cleaning/treating concentrate to which was added 0.5 part IFF 5009-S fragrance.

The concentrate was diluted 16 times with water to make a cleaning/treating composition. Soiled tufted loop pile nylon carpeting cleaned with this composition shows oil repellency of 3, a "good" water repellency and excellent soiling resistance. A carpet sample was cleaned and treated with the composition of this example and an identical carpet sample was cleaned and treated with a control composition which lacked the fluorochemical amine adduct. When both test samples were placed in a heavy pedestrian traffic situation, examination after one week showed the carpet treated according to the invention to be cleaner.

EXAMPLE 3

The fluorochemical amine, m-aminophenol-perfluorooctane sulfonate, (50 parts) was dissolved with stirring in 140 parts "Butyl Cellosolve" at 60° C., producing a clear solution. Then 25 parts TCPA was added with stirring and heating to 80° C. until reaction was complete. The reaction mixture was reduced in temperature to 60°-65° C. and 20 parts concentrated ammonium hydroxide (28% $NH_3$) was added followed immediately by 430 parts of deionized water and 4 parts of "Versenol 120" chelating agent solution. A clear solution was obtained, to which was added 150 parts "Richonol A" detergent, 657 parts of 10% styrene maleic acid copolymer ("SMA 3000") ammonium salt solution in water, 6 parts fluorochemical surfactant "FC-128", 1.5 part fragrance, and water sufficient to bring the total to 1500 parts.

One part of the resultant composition was diluted with two parts distilled water to give a solution which was placed in a conventional 12 ounce aerosol can with about 10% by weight of isobutane aerosol propellent. The aerosol shampoo was sprayed upon the surface of a 2×2 ft. soiled test sample of nylon carpeting, and the carpet cleaned by utilizing a sponge mop applicator to work the carpet surface. Another soiled carpet sample, the same type and size, was cleaned in the same manner with a prior art composition known as "New Johnson's Glory". Both cleaned samples were dried, and placed in a heavy pedestrian traffic situation. After one week, the sample treated with the composition according to the invention was considerably cleaner than that treated with the "New Johnson's Glory". Upon subsequent cleanings, the carpet treated according to the invention cleaned much easier than the carpet treated with the "New Johnson's Glory".

EXAMPLE 4

50 parts of m-aminophenol-perfluorooctane sulfonate was first dissolved in 140 parts "Butyl Cellosolve" at 60° C. and 18 parts TCPA was added with continued stirring and heating to about 80° C. until the reaction was complete. The reaction mixture was cooled to about 60°-65° and 20 parts concentrated ammonium hydroxide solution (28% $NH_3$) was added followed immediately by 218 parts deionized water, 337.5 parts 10% solution of styrene/maleic anhydride copolymer ("SMA 3000") hydrolyzed with ammonia, 135 parts "Richonol" A detergent, 4.5 parts fluorochemical surfactant ("FC 128") and 18.0 parts organic solvent ("Super Hiflash Naphtha"), producing a cleaning/treating concentrate.

Two 30 cm by 65 cm new nylon carpet test samples from the same carpet lot were cleaned, one sample with 100 ml of "CHEMSPEC 161" soil retardant carpet shampoo at the recommended dilution of 16:1 and the other sample with a solution consisting of 1 part of the concentrate described above and 8 parts water. After drying, the two samples were used in a heavy pedestrian traffic solution for over 2 weeks. The sample cleaned with composition of the invention described above had a "good" water repellency, and an oil repellency of 4 and appeared cleaner both before and after vacuuming than the sample cleaned with the "CHEMSPEC No. 161" rug shampoo.

After vacuuming, equal amounts of the following common household items which cause stains were applied over each treated carpet sample in the order shown:

red dyed vegetable oil
salad dressing
mustard
ketchup

These household items were allowed to stand on the carpet samples for over one hour, and then the excess was carefully removed with a spatula and the carpet surface blotted with an absorbent cloth. The remaining residue was removed by shampooing one test sample with 100 ml of a solution consisting of 1 part "CHEMSPEC 161" shampoo concentrate and 16 parts water. Immediately after cleaning both carpet samples appeared to be free of stains, but after drying at room temperature for about 12 hours, the sample shampooed with the composition of the invention appeared cleaner than the sample shampooed with the "CHEMSPEC 161" shampoo.

When the dried samples were placed in a heavy pedestrian traffic situation for twenty-four hours, severe soiling was noticed on the "CHEMSPEC 161" cleaned sample, especially in the areas stained as described above. The sample treated with the composition of this example looked clean over its entire surface with the exception of a very small portion of the area where the salad dressing stain had been placed. Fifteen days later the sample treated with the composition of this example was dramatically cleaner than the other sample.

EXAMPLE 5

"Butyl Cellosolve" (140 parts) and 50 parts of m-aminophenol perfluorooctane sulfonate were charged in a 3 neck flask fitted with a mechanical stirrer, thermometer and heating mantle, the contents raised to 60° C. with stirring until they became clear. Then, 25 parts TCPA was added with continued stirring and heating to about 80° C., maintaining this temperature until the solution became clear. The temperature of the flask contents was then lowered to about 60°-65° and 20 parts concentrated ammonium hydroxide solution (28% $NH_3$) was added, followed immediately by 521 parts deionized water, 4 grams of "Versenol 120" chelating agent solution and 0.5 part fragrance, producing a treatment concentrate.

EXAMPLE 6

Four 12×12 inch samples of new nylon tufted loop pile carpet (identified as A-D herein) were sprayed with a test solution consisting of 50 grams of the solutions diluted as shown below. The solutions consisted of 1 part of the concentrate of Example 5 diluted with the amount of water shown in the following table.

| Carpet Sample | Volumes of Water |
|---|---|
| A | 4 |
| B | 10 |
| C | 20 |
| D | 40 |

After drying at room temperature, each of the treated carpet samples had an oil repellency of 6 and "good" to "excellent" water repellency.

EXAMPLE 7

The concentrate of Example 5 was diluted with 4 volumes of water and the resultant solution was applied by means of an electric motor driven sprayer onto the surface of nylon loop pile carpet which had been used for some time as an entryway floor covering for the employee entrance of a large office building, at about 320 $g/m^2$ solution, producing an add-on weight of about 6.4 $g/m^2$. The next day the carpet showed "excellent" water repellency and an oil repellency of 5-6. One month later (after an estimated pedestrian traffic of 60,000 pedestrian passes) water repellency was still "excellent" and oil repellency was 6 at the edge and 4 in the main traffic lane.

EXAMPLE 8

The concentrate described in Example 5 was diluted 4 times with water and the resultant solution was sprayed at 215 $g/m^2$ with a mechanical sprayer over the surface of wool carpet which had been used for some time in an executive office area, resulting, after overnight drying, in a dried add-on weight of 4.3 $g/m^2$. Initially, the carpet showed "excellent" water repellency and an oil repellency of 6. After two months of use the repellency results were unchanged.

EXAMPLE 9

The concentrate described in Example 5 was diluted 4 times with water and the resultant solution was sprayed at 215 $g/m^2$ over the surface of a nylon carpet which had been used for some time in a men's rest room in a large office building, resulting in a dried add-on weight of 3.2 $g/m^2$. For up to 2 months later, the carpet showed "excellent" water repellency and an oil repellency of 5. The more heavily used area of the carpet (near the entrance) showed an oil repellency of 2 and "good" water repellency.

EXAMPLE 10

150 parts "Butyl Cellosolve" was mixed with 50 parts of the fluorochemical amine, m-amino-phenol perfluorooctane sulfonate, at 50° C., until a clear solution developed. Then, 18 parts TCPA was added with continued mixing and heating to 70° C. until the resultant solution cleared. Heating was discontinued and 26 parts concentrated ammonium hydroxide (28% $NH_3$) was added with stirring, followed by a mixture of 200 parts distilled water, 4 parts "Versenol-120", 340 parts 10% styrene/maleic anhydride copolymer "SMA-3000", ammonia neutralized, aqueous solution, 200 parts "Richonol A" detergent solution, 18 parts "Super Hi-flash Naphtha" organic solvent, 500 parts distilled water and 4 parts fluorochemical surfactant ("FC-128"), giving a clear cleaning/treating solution.

One half of a 30 cm×60 cm sample of new nylon loop pile carpeting was shampooed with 50 ml of Johnson's "Rugbee" shampoo at the recommended dilution. The remaining half was shampooed with 50 ml of the solution described above. The carpet samples were allowed to dry overnight at room temperature, then soiled artificially.

The artificial soiling involved securing carpet samples to the inside walls of a cylinder which contains 100 small ceramic cylinders and a soiling formulation, and rotating the cylinder at 42 revolutions per minute for 20 minutes. The cylinder was 33.3 cm high and has an inside diameter of 24.9 cm. The carpet samples were ordinarily secured to the inside walls of the cylinder with double-coated pressure-sensitive adhesive. The small ceramic cylinders were 1.9 cm by 1.9 cm in size and weighed about 23 grams each.

The soiling formulation used in the soiling test comprised:

| | Parts |
|---|---|
| Peat Moss | 70 |
| Gray Portland Cement (Type 1) | 30 |
| Silica gel (200 mesh) | 30 |
| Clay | 30 |
| Sodium chloride (about 80 mesh) | 7 |
| Gelatin | 7 |
| Carbon black | 23 |
| Red iron oxide | 1 |
| Stearic acid | 3.2 |
| Oleic acid | 3.2 |
| Peanut oil | 6 |
| Lanolin | 2 |

The half treated according to the invention looked cleaner than the untreated half both before and after vacuuming. Then each half again was shampooed with 60 ml of the shampoos previously used and observations made. The half treated according to the invention cleaned easier and cleaner than "Rugbee"-treated half using the same technique and effort. When dried, the carpet half treated with the composition according to the invention had a "good" water repellency and had an oil repellency of 2-3. The remaining half cleaned with the Johnson's "Rugbee" had a "poor" water repellency and a zero oil repellency.

EXAMPLE 11

In this example isopropyl alcohol was used as the organic solvent and sodium hydroxide as the neutralizing base. 200 parts of isopropyl alcohol and 50 parts of the fluorochemical amine described in Example 1 were heated with stirring to about 60° C., and 25 parts TCPA were added with additional stirring heating to 75° C. Within 30 minutes the mixture became clear, indicating completion of the reaction. After cooling the resultant solution to 50° C., 3.6 parts of sodium hydroxide in 50 parts water were added, followed by a mixture of 4 parts "Versenol 120", 0.5 part of fragrance and 283 parts of deionized water. The resultant solution was heated to 75°-80° C. until a clear shampoo concentrate was formed.

The concentrate was diluted with 10 volumes of water and the diluted solution sprayed on nylon carpet at about 540 g of spray/m² and the treated carpet allowed to dry at room temperature. Repellency testing showed water repellency to be "excellent" and an oil repellency of 6.

EXAMPLE 12

The fluorochemical compound active material in the carpet treatment described below was the ammonium salt of a half ester derived from chlorendic anhydride and a fluorochemical alcohol. Sixty parts of the fluorochemical alcohol, $C_8F_{17}SO_2N(C_2H_5)CH_2CH_2OH$, (0.1 mole), and 50 parts of chlorendic anhydride (0.13 mole) were melted together at 140°-150° C. for 30 minutes, producing a homogeneous glassy melt. "Butyl Cellosolve" (55 parts) was added to the melt and the mixture heated at 140° C. for an additional 10 minutes with mixing. The mixture was cooled to 60°-65° and 30 parts concentrated ammonium hydroxide (28% $NH_3$) was added followed by 355 parts deionized water, producing a clear treatment concentrate which was diluted with 10 volumes of water for use.

The diluted treatment solution was applied to test samples of nylon and acrylic carpet (both looped pile construction), producing on each a dried add-on weight of 5.4 g/m². After drying both test carpet samples showed "good" water repellency and an oil repellency of 4. Side by side artificial soiling tests with control untreated carpet samples showed the antisoiling ability of the treated carpet samples to be much superior to that of the untreated controls.

EXAMPLE 13

A carpet treatment based on the reaction product of a fluorochemical amine and a fluorochemical alcohol with chlorendic anhydride in a one step process. Thirty parts of the fluorochemical alcohol, $C_8F_{17}SO_2N(C_2H_5)CH_2CH_2OH$, (0.05 mole) was placed in a 1,000 ml "Pyrex" glass flask equipped with a thermometer and stirrer and a heating mantle and heated to 100° C. with stirring. Fifty parts chlorendic anhydride (0.13 mole) was added with continued stirring and heating to about 140° C. for 30 minutes. Thereafter, the flask contents were cooled to 90° C. and a solution of 30 parts

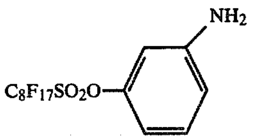

in 150 parts "Butyl Cellosolve" added, resulting in a reduction in temperature to 80° C. After maintaining an 80° C. temperature about 10 minutes, the flask contents were cooled to about 65° C. and 25 parts concentrated ammonium hydroxide (28% $NH_3$) added followed immediately by 315 parts of distilled water, producing a clear treatment concentrate which was diluted with 10 volumes of water for use.

The diluted treatment was applied over the surface of an "Antron" nylon looped pile carpet sample, after drying providing a dried add-on weight of 5.4 g/m$^2$. The treated carpet had a "good" to "excellent" water repellency and an oil repellency of 4. Artificial soiling of the treated carpet sample and an untreated control revealed that the treated sample had excellent antisoiling properties.

EXAMPLES 14–56

Textile treating compositions Examples 14–56 were prepared of materials shown in the following table and tested for repellency on new tufted nylon carpeting which had been exhaustively cleaned. Shampooing was with "Triple S" rug and upholstery shampoo manufactured by Standardized Sanitation Systems, Inc. The shampooed carpet samples were dried at room temperature for at least 12 hours, cut into 7 to 10 cm wide strips, placed in a household automatic washing machine for full cycle utilizing water only to rinse, and dried in a household dryer.

Before repellency testing, the stripped test samples had a zero oil repellency and a "poor" water repellency. The treatments of Examples 14–56, after being dried at room temperature for about 12 hours produced a dry add-on weight on the order of 3 to 6.5 grams per sq. m.

| | Reactants (moles) | | | | Reaction | Neutralizing | Organic | Repellency | |
|---|---|---|---|---|---|---|---|---|---|
| Ex. | Fluorochemical | | Acid or anhydride | | solvent | base | solvent | Water | Oil |
| 14 | 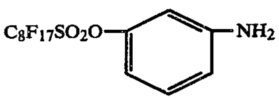 | 1.0 | tetrachlorophthalic anhydride | 1.0 | IPA[1] | NaOH | BC[2]<br>IPA | excellent | 5 |
| 15 | " | " | " | | BC | $NH_3$ | BC | " | 6 |
| 16 | " | " | " | | IPA | diethanol amine | IPA | fair | 4 |
| 17 | " | " | " | | ethanol | NaOH | ethanol | excellent | 5 |
| 18 | " | " | " | | IPA | KOH | IPA<br>BC | " | 6 |
| 19 | " | " | tetrabromophthalic anhydride | 1.0 | BC | $NH_3$ | BC | " | 4 |
| 20 | " | " | chlorendic anhydride | 1.0 | IPA | $NH_3$ | IPA | " | 5 |
| 21 | " | " | " | | BC | $NH_3$ | BC | " | 5 |
| 22 | " | 1.0 | nitrophthalic anhydride | 1.0 | DMF[3] | $NH_3$ | BC[2] | good[4]<br>fair | 4 |
| 23 | " | 1.0 | 4-nitrophthalic anhydride | 1.0 | BC | $NH_3$ | BC<br>acetone | good[4]<br>fair | 2<br>5 |
| 24 | " | 0.9 | 1,2-cyclohexane dicarboxylic acid anhydride | 1.0 | BC | $NH_3$ | BC | good[4]<br>fair | 4 |
| 25 | " | 2.0 | benzophenone tetracarboxylic acid dianhydride | 1.0 | BC | diethanol amine | BC | excellent | 5 |
| 26 | " | 1.0 | norbornene dicarboxylic acid anhydride | 1.0 | BC | $NH_3$ | BC | good | 5 |
| 27 | " | 1.0 | phthalic anhydride | 1.0 | DMF | $NH_3$ | IPA[1] | fair[4]<br>poor | 3<br>4 |
| 28 | " | 1.0 | naphthalic 1,8-dicarboxylic acid anhydride | 1.0 | DMF | $NH_3$ | BC | good[4]<br>poor | 5 |
| 29 | " | 2.0 | pyromellite dianhydride (PMDA) | 1.0 | DMF[3] | $NH_3$ | BC[2] | good | 4 |
| 30 | " | 1.0 | maleic anhydride | 1.0 | DMF | $NH_3$ | IPA[1] | good[4]<br>poor | 5 |
| 31 | " | 1.0 | "SMA 1000"[5] | 2.0 | BC | $NH_3$ | BC | good | 3 |
| 32 | " | 1.0 | "SMA 2000"[6] | 1.0 | BC | $NH_3$ | BC | good | 3 |
| 33 | " | 1.0 | "SMA 2000"[5] | 2.0 | BC | $NH_3$ | BC | excellent[4]<br>good | 2 |
| 34 | " | 1.0 | "SMA 3000"[5] | 1.0 | BC | $NH_3$ | BC | excellent [4]<br>goood | 2 |
| 35 | " | 1.0 | "Gantrez AN 139"[8] | 1.0 | DMF | $NH_3$ | BC | good[4]<br>fair | 1<br>2 |
| 36 | " | 1.0 | TCPA | 0.7 | DMF | $NH_3$ | BC | excellent | 5 |
| 37 | $C_8F_{17}SO_2N-CH_2CH_2NH_2$<br>\|<br>$CH_3$ | 1.0 | chlorendic anhydride | 1.0 | BC[2] | $NH_3$ | BC | good | 5 |
| 38 | " | 1.0 | tetrachlorophthalic | | | | BC/ | | |

-continued

| Ex. | Reactants (moles) Fluorochemical | | Acid or anhydride | | Reaction solvent | Neutralizing base | Organic solvent | Repellency Water | Oil |
|---|---|---|---|---|---|---|---|---|---|
| | | | anhydride | 1.0 | BC | $NH_3$ | acetone | good | 4 |
| 39 | $C_8F_{17}SO_2NHCH_2CH_2NH_2$ | 1.0 | " | 1.0 | N-methyl pyrolidone | triethyl amine | BC | good | 4 |
| 40 | " | 1.0 | chlorendic anhydride | 1.0 | DMF[3] | $NH_3$ | BC | good | 4 |
| 41 | 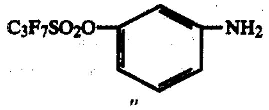 | 1.0 | " | 1.0 | BC | $NH_3$ | BC | good | 1 |
| 42 | " | 1.0 | tetrachlorophthalic | | | | | good[4] | 1 |
| | | 1.0 | anhydride | a.0 | BC | $NH_3$ | BC | fair | 2 |
| 43 | " | 2.0 | " | 1.0 | BC | $NH_3$ | BC | good[4] | 2 |
| | | | | | | | | fair | 3 |
| 44 | 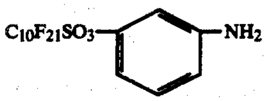 | 1.0 | chlorendic anhydride | 1.0 | BC[2] | $NH_3$ | BC | excellent | 4 |
| 45 | 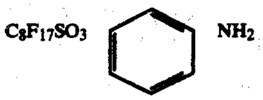 | 1.0 | "SMA 3000"[7] | 2.0 | BC | $NH_3$ | BC | good | 2 |
| 46 | $C_2H_5$<br>\|<br>$C_8F_{17}SO_2N$—$C_2H_4$—NH—$C_2H_4$—$NH_2$ | 0.8 | tetrachlorophthalic anhydride | 1.0 | BC | $NH_3$ | BC | excellent | 5 |
| 47 | 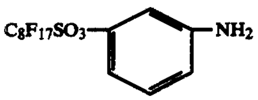 | 1.0 | "SMA 1000"[5] | 3.0 | BC | $NH_3$ | BC | excellent[4] | |
| | | | | | | | | good | 2 |
| 48 | $C_6F_{13}SO_2N$—$CH_2CH_2OH$<br>\|<br>$CH_3$ | 1.0 | chlorendic anhydride | 1.25 | none | $NH_3$ | BC | good | 2 |
| 49 | $C_8F_{17}$—$SO_2N$—$CH_2CH_2OH$<br>\|<br>$C_2H_5$ | 1.0 | " | 1.25 | N-methyl pyrolidone triethylamine | $NH_3$ | BC | fair | 4 |
| 50 | $C_8F_{17}SO_2N$—$CH_2CH_2OH$<br>\|<br>$C_2H_5$ | 1.0 | cyclohexane 1,2-dicarboxylic acid anhydride | 1.3 | none | $NH_3$ | BC[2] | fair | 4 |
| 51 | " | 1.0 | chlorendic anhydride | 1.25 | " | $NH_3$ | BC | good | 4 |
| 52 | $C_8F_{17}$—$SO_2$—N—$CH_2CH_2OH$<br>\|<br>$C_4H_9$ | 1.0 | " | | " | $NH_3$ | IPA[1] | good | 2 |
| 53 | $C_8F_{17}SO_2$—N—$(CH_{210}OH$<br>\|<br>$C_2H_5$ | 1.0 | cyclohexane dicarboxylic acid anhydride | 1.25<br>1.3 | " | $NH_3$ | BC | fair | 5 |
| 54 | " | 1.0 | tetrachlorophthalic anhydride | 1.0 | DMF[3] | $NH_3$ | BC | good | 4 |
| 55 | $C_8F_{17}SO_2N$—$CH_2CH_2OH$<br>\|<br>$C_2H_5$ | 1.0 | "SMA 1000"[5] | 2.0 | DMF | $NH_3$ | BC | excellent[4] | 1 |
| | | | | | | | | fair | 3 |
| 56 | " | 1.0 | "SMA 1000"[5] | 4.5 | DMF | $NH_3$ | BC | fair | 2 |

[1]isopropyl alcohol
[2]"Butyl Cellosolve"
[3]dimethyl formamide
[4]dried in oven at 120° C.
[5]styrene/maleic anhydride (1:1) copolymer
[6]styrene/maleic anhydride (2.1) copolymer
[7]styrene/maleic anhydride (3:1) copolymer
[8]copolymer of maleic anhydride and methyl vinyl ether

What is claimed is:

1. A fluorochemical compound having the formula $(R_fQ)_e(XCO)_mA(COOM)_p$ where $R_f$ is fluorinated aliphatic radical having from three to twenty carbon atoms and containing about 40–78 weight percent carbon-bonded fluorine, "Q" is a divalent linking radical selected from the group consisting of $-(CH_2)_n-$, $-SO_2NR_1(CH_2)_n-$, $-(CH_2)_nCOOCH_2CH_2-$, $-SO_2NR_1(CH_2CH_2O)_nCH_2CH_2$, $-SO_2(C_2H_5)C_2H_4NHC_2H_4-$ and $-SO_2$

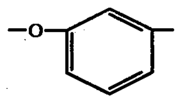

wherein "$R_1$" is hydrogen or a lower alkyl group having from about 1 to 14 carbon atoms and "n" is an integer from about 1 to 15, "M" is a cation selected from $NH_4$+, Na+, K+, Li+, H+ or is a protonated alkyl amine having from 1-6 carbon atoms in the alkyl group, "A" is a polyvalent organic radical having a valency of m+p and is the residue obtained by eliminating the carboxyl groups of a polybasic organic acid or an organic anhydride and is selected from the group consisting of maleic, succinic, phthalic, tetrachlorophthalic, chlorendic, tetrabromophthalic, 3-nitrophthalic, 4-nitrophthalic, cis 1,2-cyclohexane dicarboxylic, 5-norborene-2,3-dicarboxylic, 1,8-naphthalene dicarboxylic and benezophenone tetracarboxylic and pyromellitic, "X" is NR (wherein R is hydrogen or an alkyl group of from 1 to 14 carbon atoms), or N and "e", "p" and "m" are integers of 1 or 2.

2. The compound of claim 1 wherein "A" is the residue of chlorendic anhydride.

3. A fluorochemical compound having the formula

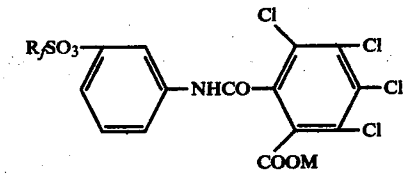

wherein $R_f$ is $C_8F_{17}$ and M is K+, Na+ or $NH_4$+.

4. A fluorochemical compound having the formula

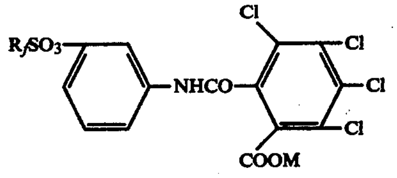

wherein $R_f$ is a fluorinated aliphatic radical having from three to twenty carbon atoms and containing about 40-78 weight percent carbon bonded fluorine and M is K+, Na+ or $NH_4$+.

* * * * *

UNITED STATES PATENT AND TRADEMARK OFFICE

CERTIFICATE OF CORRECTION

PATENT NO. : 4,160,777

DATED : July 10, 1979

INVENTOR(S) : Basil L. Loudas

It is certified that error appears in the above-identified patent and that said Letters Patent are hereby corrected as shown below:

In the Specification:

Ex. 22 (Cols. 15-16, Ex. 22, 4th col.), "nitrophthalic" should read --3-nitrophthalic--.

Ex. 33 (Cols. 15-16, Ex. 33, 4th col.), " "SMA 2000"[5]" should read --"SMA 2000"--.

Ex. 34 (Cols. 15-16, Ex. 34, 4th col.), " "SMA 3000"[5]" should read --"SMA 3000"[7]--.

Ex. 42 (Cols. 17-18, Ex. 42, 4th, 5th and 6th cols.), "1.0 anhydride a.0" should read --anhydride 1.0--.

Ex. 53 (Cols. 17-18, Ex. 53, 2nd col.) "$(CH_{210}OH$" should read --$(CH_2)_{10}OH$--.

Ex. 53 (Cols. 17-18, Ex. 53, 4th col.) "cyclohexane" should read --cyclohexane 1,2- --.

Signed and Sealed this

*Twelfth* Day of *February 1980*

[SEAL]

*Attest:*

SIDNEY A. DIAMOND

*Attesting Officer*

*Commissioner of Patents and Trademarks*